United States Patent [19]
Koch et al.

[11] 3,932,290
[45] Jan. 13, 1976

[54] PHOSPHORUS-CONTAINING FRICTION MODIFIERS FOR FUNCTIONAL FLUIDS

[75] Inventors: Frederick William Koch, Willoughby Hills; Jerry Lee Musser, Chardon, both of Ohio

[73] Assignee: The Lubrizol Corporation, Cleveland, Ohio

[22] Filed: Oct. 4, 1973

[21] Appl. No.: 403,373

[52] U.S. Cl. .................. 252/49.8; 252/78; 260/970
[51] Int. Cl.$^2$ .......................................... C10M 1/10
[58] Field of Search ............. 252/49.8, 78, 49.8 TD

[56] References Cited
UNITED STATES PATENTS

| | | | |
|---|---|---|---|
| 2,856,369 | 10/1958 | Smith et al. | 252/49.8 X |
| 3,166,504 | 1/1965 | Krukziener et al. | 252/49.8 X |
| 3,247,113 | 4/1966 | Hasseroot et al. | 252/49.8 |
| 3,267,149 | 8/1966 | Garner | 252/49.8 X |
| 3,502,749 | 3/1970 | Goren et al. | 252/49.8 X |
| 3,591,501 | 7/1971 | Olszewski et al. | 252/49.8 |
| 3,600,470 | 8/1971 | Lewis | 252/49.8 |
| 3,626,035 | 12/1971 | Ernst | 252/49.8 X |
| 3,748,363 | 7/1973 | Maier | 252/49.8 X |

FOREIGN PATENTS OR APPLICATIONS

| | | | |
|---|---|---|---|
| 1,098,315 | 1/1968 | United Kingdom | 252/49.8 |
| 1,203,648 | 8/1970 | United Kingdom | 252/49.8 |

Primary Examiner—Delbert E. Gantz
Assistant Examiner—Andrew H. Metz
Attorney, Agent, or Firm—James W. Adams, Jr.; William H. Pittman

[57] ABSTRACT

Compositions prepared by the reaction of a di-(lower alkyl) phosphite with a $C_{10-20}$ epoxide in the presence of a strongly alkaline reagent are useful as friction-reducing additives in functional fluids, especially automatic transmission fluids.

3 Claims, No Drawings

PHOSPHORUS-CONTAINING FRICTION MODIFIERS FOR FUNCTIONAL FLUIDS

This invention relates to new compositions of matter suitable for use as friction reducing additives in functional fluids, and to functional fluids containing the same. More particularly, it relates to compositions prepared by reacting at least one phosphorus compound of the formula

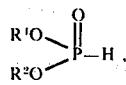

wherein each of $R^1$ and $R^2$ is a lower alkyl or substituted lower alkyl radical, with at least one epoxide of the formula

wherein $R^3$ is an alkyl radical having 10–20 carbon atoms.

The development of the functional fluids for power transmission, including such materials as hydraulic fluids and automatic transmission fluids, has necessitated the development of new additives to improve power transmission properties. One of the properties which must frequently be changed is the frictional nature of the liquid. Thus, it is sometimes preferred that the fluid have a coefficient of friction substantially lower than that of the base oil which is its major component. Improved friction-reducing additives have therefore been of considerable interest.

A principal object of the present invention, therefore, is to produce new phosphorus-containing compositions of matter.

A further object is to produce composition which decrease the coefficient of friction of a lubricant or functional fluid when incorporated therein.

Another object is to provide new fluid suitable for power transmission, especially in automatic transmissions.

Still another object is to provide automatic transmission fluids and other functional fluids having a low coefficient of friction.

Other objects will in part be obvious and will in part appear hereinafter.

As previously indicated, the compositions of this invention are prepared by the reaction of a phosphite diester with an epoxide. The phosphite diester is usually a di-(lower alkyl) phosphite. The term "lower alkyl" as used herein means an alkyl radical containing not more than 7 carbon atoms.

Substituted lower alkyl radicals are considered fully equivalent to the lower alkyl radicals and to be part of this invention. By "substituted" is meant radicals containing substituents which do not alter significantly the character or reactivity of the radical. Examples of such substituents are:

Halide (fluoride, chloride, bromide, iodide)
Hydroxy
Ether (especially lower alkoxy)
Keto
Ester (especially lower carbalkoxy)
Nitro
Thioether
Sulfoxy
Sulfone In general, no more than about one such substituent group will be present in the radical.

The epoxide is one which contains about 12–22 carbon atoms. Commercial mixtures of such epoxides are available and their use is contemplated as part of this invention.

The proportions of the two reactants are not critical, since any excess of either reactant will merely remain in the product without substantially affecting its properties. It is usually preferred to use approximately equimolar amounts of the two, or a slight excess of the epoxide; for example, about 1.0–1.5 moles of the epoxide per mole of dialkyl phosphite.

The reaction is carried out in the presence of a strongly alkaline reagent, usually an alkali metal or an alkyl, alkoxide, amide or the like derived therefrom. A very small amount of alkaline reagent is generally needed, usually about 0.01–0.5% based on the total weight of the reactants.

The reaction is carried out by merely heating the mixture to a temperature above about 100°C. and below the decomposition temperature thereof, generally about 150°–225°C. It is preferably effected in an atmosphere of an inert gas such as nitrogen. Inert diluents may be used but are usually not necessary.

Following the reaction, volatiles may be removed as by stripping, usually under vacuum, and the residue is filtered to afford the desired product. If necessary, the product may be purified by conventional means, but it is usually possible to employ it for the purposes of this invention without purification.

The compositions of this invention are probably mixtures rather than simple chemical compounds, and thus it is possible to define them completely only in terms of the method for their preparation. However, there is evidence that the reaction between the phosphite and the epoxide is chiefly a simple addition reaction and that the predominant product has the formula

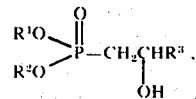

wherein $R^1$, $R^2$ and $R^3$ are as previously defined. Compounds of this formula may be separated from other materials present in the product by conventional separation means such as chromatography, and such compounds are contemplated as part of this invention.

The preparation of the compositions of this invention is illustrated by the following examples. All parts and percentages are by weight.

EXAMPLE 1

A mixture of 194 parts (1 mole) of di-n-butyl phosphite, 239 parts (1 mole) of an epoxide derived from a commercial mixture of $C_{14}$ and $C_{16}$ straight chain α-olefins, and 0.2 part of sodium methoxide is heated for eight hours at 190°–200°C. An additional 60 parts (0.25 mole) of epoxide are added and heating is continued at 200°–205°C. for 8 hours. Volatile materials are then removed by vacuum stripping at 150°C. and the residue is filtered through a filter aid material to yield the desired product which contains 6.28% phosphorus.

EXAMPLE 2

A mixture of 776 parts (4 moles) of di-n-butyl phosphite and 1195 parts (5 moles) of the epoxide of Example 1 is purged with nitrogen, and 4.6 parts of sodium metal is added. The mixture is heated at 160°–170°C. for 10 hours under nitrogen, and is then filtered through a filter aid material. The filtrate, which is the desired product, contains 6.30% phosphorus.

EXAMPLE 3

The procedure of Example 2 is repeated, except that di-isohexyl phosphite is substituted on an equimolar basis for the di-n-butyl phosphite. A similar product is obtained.

EXAMPLE 4

The procedure of Example 2 is repeated, except that the epoxide used is an epoxide derived from propene tetramer. A similar product is obtained.

As previously mentioned, the compositions of this invention are useful as friction-modifying additives in functional fluids. As such, they can be employed in a variety of lubricating compositions based on diverse oils of lubricating viscosity, including natural and synthetic lubricating oils and mixtures thereof. The compositions contemplated include principally automatic transmission fluids, transaxle lubricants, hydraulic fluids and the like, but other lubricating oil and grease compositions can also benefit from the incorporation of the present compositions.

Natural oils include animal oils and vegetable oils (e.g., castor oil, lard oil) as well as solvent-refined or acid-refined mineral lubricating oils of the paraffinic, naphthenic, or mixed paraffinic-naphthenic types. Oils of lubricating viscosity derived from coal or shale are also useful base oils. Synthetic lubricating oils include hydrocarbon oils and halo-substituted hydrocarbon oils such as polymerized and interpolymerized olefins (e.g., polybutylenes, polypropylenes, propylene-isobutylene copolymers, chlorinated polybutylenes, etc.); alkylbenzenes (e.g., dodecylbenzenes, tetradecylbenzene, dinonylbenzenes, di-(2-ethylhexyl) benzenes, etc.); polyphenyls (e.g., biphenyls, terphenyls, etc.); and the like. Alkylene oxide polymers and interpolymers and derivatives thereof where the terminal hydroxyl groups have been modified by esterification, etherification, etc., constitute another class of known synthetic lubricating oils. These are exemplified by the oils prepared through polymerization of ethylene oxide or propylene oxide, the alkyl and aryl ethers of these polyoxyalkylene polymers (e.g., methylpolyisopropylene glycol ether having an average molecular weight of 1000, diphenyl ether of polyethylene glycol having a molecular weight of 500–1000, diethyl ether of polypropylene glycol having a molecular weight of 1000–1500, etc.) or mono- and polycarboxylic esters thereof, for example, the acetic acid esters, mixed $C_3$-$C_8$ fatty acid esters, or the $C_{13}$ Oxo acid diester of tetraethylene glycol. Another suitable class of synthetic lubricating oils comprises the esters of dicarboxylic acids (e.g., phthalic acid, succinic acid, maleic acid, azelaic acid, suberic acid, sebacic acid, fumaric acid, adipic acid, linoleic acid dimer, etc.) with a variety of alcohols (e.g., butyl alcohol, hexyl alcohol, dodecyl alcohol, 2-ethylhexyl alcohol, etc.). Specific examples of these esters include dibutyl adipate, di(2-ethylhexyl) sebacate, di-n-hexyl fumarate, dioctyl sebacate, diisooctyl azelate, diisodecyl azelate, dioctyl phthalate, didecyl phthalate, dieicosyl sebacate, the 2-ethylhexyl diester of linoleic acid dimer, the complex ester formed by reacting one mole of sebacic acid with two moles of tetraethylene glycol and two moles of 2-ethylhexanoic acid, and the like. Silicon-based oils such as the polyalkyl-, polyaryl-, polyalkoxy-, or polyaryloxy-siloxane oils and silicate oils comprise another useful class of synthetic lubricants (e.g., tetraethyl silicate, tetraisopropyl silicate, tetra-(2-ethylhexyl) silicate, tetra-(4-methyl-2-tetraethyl) silicate, tetra-(p-tert-butylphenyl) silicate, hexyl-(4-methyl-2-pentoxy)-disiloxane, poly(methyl)-siloxanes, poly(methylphenyl)-siloxanes, etc.). Other synthetic lubricating oils include liquid esters of phosphorus-containing acids (e.g., tricresyl phosphate, trioctyl phosphate, diethyl ester of decane phosphonic acid, etc.), polymeric tetrahydrofurans, and the like.

In general, about 0.05–20.0 parts (by weight) of the composition of this invention is dissolved in 100 parts of oil to produce a satisfactory fluid. The invention also contemplates the use of other additives in combination with the products of this invention. Such additives include, for example, detergents and dispersants of the ash-containing or ashless type, oxidation inhibiting agents, pour point depressing agents, extreme pressure agents, color stabilizers and anti-foam agents.

The ash-containing detergents are exemplified by oil-soluble neutral and basic salts of alkali or alkaline earth metals with sulfonic acids, carboxylic acids, or organic phosphorus acids characterized by at least one direct carbon-to-phosphorus linkage such as those prepared by the treatment of an olefin polymer (e.g., polyisobutene having a molecular weight of 1000) with a phosphorizing agent such as phosphorus trichloride, phosphorus heptasulfide, phosphorus pentasulfide, phosphorus trichloride and sulfur, white phosphorus and a sulfur halide, or phosphorothioic chloride. The most commonly used salts of such acids are those of sodium, potassium, lithium, calcium, magnesium, strontium and barium.

The term "basic salt" is used to designate metal salts wherein the metal is present in stoichiometrically larger amounts than the organic acid radical. The commonly employed methods for preparing the basic salts involve heating a mineral oil solution of an acid with a stoichiometric excess of a metal neutralizing agent such as the metal oxide, hydroxide, carbonate, bicarbonate, or sulfide at a temperature above 50°C. and filtering the resulting mass. The use of a "promotor" in the neutralization step to aid the incorporation of a large excess of metal likewise is known. Examples of compounds useful as the promoter include phenolic substances such as phenol, naphthol, alkylphenol, thiophenol, sulfurized alkylphenol, and condensation products of formaldehyde with a phenolic substance; alcohols such as methanol, 2-propanol, octyl alcohol, cellosolve, carbitol, ethylene glycol, stearyl alcohol, and cyclohexyl alcohol; and amines such as aniline, phenylenediamine, phenothiazine, phenyl-β-naphthylamine, and dodecylamine. A particularly effective method for preparing the basic salts comprises mixing an acid with an excess of a basic alkaline earth metal neutralizing agent and at least one alcohol promoter, and carbonating the mixture at an elevated temperature such as 60°–200°C.

Ashless detergents and dispersants are illustrated by the interpolymers of an oil-solubilizing monomer, e.g., decyl methacrylate, vinyl decyl ether, or high molecular weight olefin, with a monomer containing polar substituents, e.g., aminoalkyl acrylate or poly-(oxyethylene)-substituted acrylate; the amine salts, amides, and imides of oil-soluble monocarboxylic or dicarboxylic acids such as stearic acid, oleic acid, tall oil acid, and high molecular weight alkyl or alkenyl-substituted succinic acid. Especially useful as ashless detergents are the acylated polyamines and similar nitrogen compounds containing at least about 54 carbon atoms as described in U.S. Pat. No. 3,272,746; reaction products of such compounds with other reagents including boron compounds, phosphorus compounds, epoxides, aldehydes, organic acids and the like; and esters of hydrocarbon-substituted succinic acids as described in U.S. Pat. No. 3,381,022.

Auxiliary extreme pressure agents and corrosion-inhibiting and oxidation-inhibiting agents are exemplified by chlorinated aliphatic hydrocarbons such as chlorinated wax; organic sulfides and polysulfides such as benzyl disulfide, bis(chlorobenzyl) disulfide, dibutyl tetrasulfide, sulfurized methyl ester of oleic acid, sulfurized alkylphenol, sulfurized dipentene, and sulfurized terpene; phosphosulfurized hydrocarbons such as the reaction product of a phosphorus sulfide with turpentine or methyl oleate; phosphorus esters including principally dihydrocarbon and trihydrocarbon phosphites such as dibutyl phosphite, diheptyl phosphite, dicyclohexyl phosphite, pentyl phenyl phosphite, dipentyl phenyl phosphite, tridecyl phosphite, distearyl phosphite, dimethyl naphthyl phosphite, oleyl 4-pentylphenyl phosphite, polypropylene (molecular weight 500)-substituted phenyl phosphite, diisobutyl-substituted phenyl phosphite; metal thiocarbamates, such as zinc dioctyldithiocarbamate, and barium heptylphenyl dithiocarbamate; Group II metal phosphorodithioates such as zinc dicyclohexylphosphorodithioate, zinc dioctylphosphorodithioate, barium di(heptylphenyl)-phosphorodithioate, cadmium dinonylphosphorodithioate, and the zinc salt of a phosphorodithioic acid produced by the reaction of phosphorus pentasulfide with an equimolar mixture of isopropyl alcohol and n-hexyl alcohol.

It is possible to form the fluids of this invention by dissolving the various additives, or oil solutions thereof, directly in a mineral oil. However, it is often more convenient to prepare additive concentrates containing two or more of the desired additives, and to dissolve these concentrates in the mineral oil to form the functional fluid.

A typical automatic transmission fluid of this invention has the following composition, all percentages being by weight:

| | |
|---|---|
| Mineral oil (ATF base) | 92.25% |
| Product of Example 1 | 0.13% |
| Polyisobutenyl succinic anhydride-polyethylene polyamine (3-7 amino groups) reaction product | 1.75% |
| Reaction product of boric acid with polyisobutenyl succinic anhydride-polyethylene polyamine reaction product | 0.67% |
| Zinc di-(isooctyl)phosphorodithioate | 0.64% |
| Tallow-substituted diethanolamine | 0.10% |
| Mixed ester-amide of maleic anhydride-styrene copolymer (12% soln. in toluene) | 1.20% |
| Hydrocarbon resin seal swelling agent | 3.00% |
| Substituted diphenylamine | 0.20% |
| Reaction product of glycidol (2 moles) with C$_{12}$ primary amine mixture (1 mole) | 0.04% |
| Silicone anti-foam agent | 0.02% |

What is claimed is:

1. A functional fluid composition comprising a major amount of a lubricating oil and a minor friction-reducing amount of the product obtained by reacting, at a temperature above about 100°C. and below the decomposition temperature of the reaction mixture, and in the presence of a strongly alkaline reagent, at least one phosphorus compound of the formula

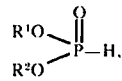

wherein each of R$^1$ and R$^2$ is a lower alkyl radical, with at least one epoxide of the formula

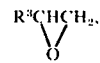

wherein R$^3$ is an alkyl radical having 10–20 carbon atoms; about 1.0–1.5 moles of said epoxide being present per mole of said phosphorus compound.

2. A composition according to claim 1 wherein the epoxide is derived from a commercial mixture of C$_{14}$ and C$_{16}$ straight chain α-olefins.

3. A composition according to claim 2 wherein R$^1$ and R$^2$ are n-butyl radicals.

* * * * *